United States Patent [19]

Kataoka et al.

[11] Patent Number: 4,751,293
[45] Date of Patent: * Jun. 14, 1988

[54] PROCESS FOR PREPARATION OF $N^6$-SUBSTITUTED 3',5'-CYCLIC ADENOSINE MONOPHOSPHATE AND SALT THEREOF

[75] Inventors: Shigehiro Kataoka; Ayako Nasu; Nobuyuki Yamaji; Motohiko Kato, all of Noda, Japan

[73] Assignee: Kikkoman Corporation, Noda, Japan

[*] Notice: The portion of the term of this patent subsequent to Jan. 28, 2003 has been disclaimed.

[21] Appl. No.: 727,062

[22] Filed: Apr. 25, 1985

[30] Foreign Application Priority Data

May 11, 1984 [JP] Japan .................. 59-93014

[51] Int. Cl.$^4$ .................. C07H 15/12; C07H 17/00
[52] U.S. Cl. .................. 536/27; 536/24; 536/26; 536/28
[58] Field of Search .................. 536/24, 26, 27, 28

[56] References Cited

U.S. PATENT DOCUMENTS 4,044,123  8/1977  Daniels et al. .................. 536/13.6
4,567,254  1/1986  Kataoka et al. .................. 536/27

FOREIGN PATENT DOCUMENTS 0116298  7/1984  Japan .................. 536/27

OTHER PUBLICATIONS

Meyer et al, "Synthesis and Biological Activity of Several 6-Substituted 9-$\beta$-D-Ribofuranosylpurine 3', 5'-Cyclic Phosphates," Biochemistry, vol. 11, No. 14, (1972).
Miller et al, "Synthesis and Enzymatic and Inotropic Activity of Some New 8-Substituted and 6,8-Disubstituted Derivatives of Adenosine Cyclic 3', 5'-Monophosphate," J. Med. Chem., 23, 242-251 (1980).

Primary Examiner—J. R. Brown
Assistant Examiner—L. Eric Crane
Attorney, Agent, or Firm—Banner, Birch, McKie & Beckett

[57] ABSTRACT

A method for the preparation of an $N^6$-substituted 3',5'-cyclic adenosine monophosphate or a salt thereof represented by the general formula

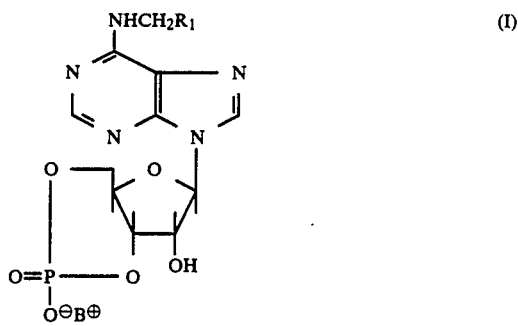

wherein $R_1$ represents a straight chain or branched chain alkyl group of 1 to 13 carbon atoms or an aromatic group and $B \oplus$ represents a hydrogen ion or an alkali metal ion, which comprises allowing a 3',5'-cyclic adenosine monophosphate or a salt thereof represented by the general formula

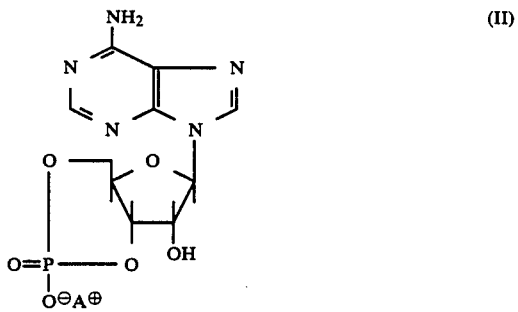

wherein $A \oplus$ represents a hydrogen ion, alkali metal ion, organic ammonium ion, or ammonium ion, to react with an aldehyde represented by the general formula

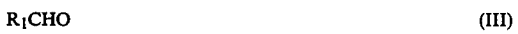

$R_1CHO$   (III)

wherein $R_1$ is as defined above, under the conditions such that pH is 7.0 or below, the temperature is $-10°$ to 120° C., and the molar ratio of the compound (II) to the compound (III) is 1:1–40, and reducing the resulting compound with a metal hydride or nascent hydrogen.

6 Claims, No Drawings

PROCESS FOR PREPARATION OF N⁶-SUBSTITUTED 3',5'-CYCLIC ADENOSINE MONOPHOSPHATE AND SALT THEREOF

BACKGROUND OF THE INVENTION

1. Field of the Invention

This invention relates to a novel method for the preparation of an $N^6$-substituted 3',5'-cyclic adenosine monophosphate (hereinafter referred to briefly as $N^6$-substituted CAMP) and a salt thereof.

2. Description of the Prior Art

The $N^6$-substituted CAMP is of high utility value as an important intermediate used in the synthesis of 6,8-disubstituted CAMP (U.S. Pat. No. 4,058,659) which has excellent pharmacological activities including antiinflammative, platelet aggregation inhibitory, hypotensive, and cardiotonic actions.

For the preparation of an $N^6$-substituted 8-thiobenzyl-CAMP, as an example among 6,8-disubstituted derivatives of CAMP, from an $N^6$-substituted CAMP, there is known a method described in Journal of Medicinal Chemistry, Vol. 23, 242-251 (1980).

Conventionally known methods of producing an $N^6$-substituted CAMP include a method which comprises deamination of CAMP with a nitrite to form inosine 3',5'-cyclic phosphate followed by chlorination with phosphorus oxychloride to 6-chloropurine-9-β-D-ribofuranosyl-3',5'-cyclic phosphate which is then reacted with an alkylamine to yield an $N^6$-substituted CAMP [Biochemistry, Vol. 11, 2704-2709 (1972)] and another one which comprises the reaction of CAMP with a halide to form a 1-substituted CAMP followed by Dimroth rearrangement in an alkali solution to yield an $N^6$-substituted CAMP. Both of these methods, however, have disadvantages of complicated procedures, possible by-product formation, and low yields.

SUMMARY OF THE INVENTION

The present inventors carried out an extensive study to overcome the above difficulties. This invention is predicated upon the finding that an $N^6$-substituted CAMP or a salt thereof can be prepared with a high efficiency by allowing CAMP or a salt thereof to react with an aldehyde and then reducing the reaction product.

The primary object of this invention is to provide an efficient method for the preparation of an $N^6$-substituted CAMP or a salt thereof.

According to this invention, there is provided a method for the preparation of an $N^6$-substituted 3',5'-cyclic adenosine monophosphate or a salt thereof represented by the general formula

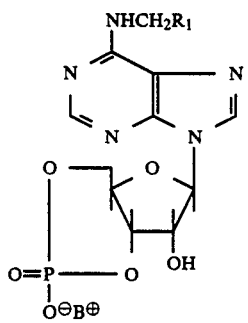   (I)

wherein $R_1$ represents a straight chain or branched chain alkyl group of 1 to 13 carbon atoms or an aromatic group and $B^⊕$ represents a hydrogen ion or an alkali metal ion, which comprises allowing a 3',5'-cyclic adenosine monophosphate or a salt thereof represented by the general formula

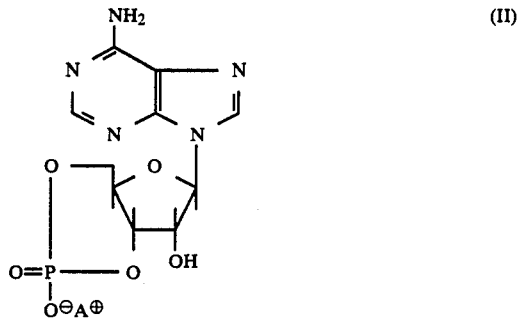   (II)

wherein $A^⊕$ represents a hydrogen ion, alkali metal ion, organic ammonium ion, or ammonium ion, to react with an aldehyde represented by the general formula $$R_1CHO \qquad (III)$$

wherein $R_1$ is as defined above, under the conditions such that pH is 7.0 or below, the temperature is $-10°$ to $120°$ C., and the molar ratio of the compound (II) to the compound (III) is 1:1–40, and reducing the resulting compound with a metal hydride or nascent hydrogen.

DETAILED DESCRIPTION OF THE INVENTION

CAMP or a salt thereof (II) used as the starting material in the present method is prepared, for example, in the following manner. A bacterium of the genus Microbacterium, which is capable of producing CAMP from adenine, xylose or ribose, and an inorganic phosphate, is cultivated in a medium containing adenine xylose or ribose, and an inorganic phosphate, and CAMP is collected from the cultured medium (Japanese Patent Publication No. 34/1972). Furthermore, when the isolated free CAMP is reacted with hydroxides, carbonates, or hydrogen carbonates of alkali metals or alkaline earth metals, organic amines, preferably trialkylamines, there are formed in the part of CAMP molecule, where phosphoric acid moiety combined, alkali metal salts, e.g. sodium salt and potassium salt, alkaline earth metal salts, e.g. calcium salt and magnesium salt; organic ammonium salts, e.g. triethylamine salt and tributylamine salt.

As the substituent $R_1$ in the aldehyde represented by the general formula (III), mention may be made of straight chain or branched chain alkyl groups having 1 to 13 carbon atoms such as, for example, methyl, ethyl, propyl, isopropyl, butyl, isobutyl, pentyl, isopentyl, hexyl, isohexyl, heptyl, octyl, nonyl, decyl, undecyl, and tridecyl groups; and aromatic groups such as, for example, phenyl, furyl, tolyl, hydroxyphenyl, methoxyphenyl, and chlorophenyl groups.

In carrying out the method of this invention, at first a compound of formula (II) is allowed to react with an aldehyde of formula (III) in a solvent to form a corresponding imine compound. Suitable solvents include water, alcohols, e.g. methanol and ethanol; ethers, e.g. tetrahydrofuran and dioxane; amides, e.g. dimethylformamide and dimethylacetamide; organic carboxylic acids and esters thereof, e.g. acetic acid, ethyl acetate, and butyric acid; and halogenated hydrocarbons, e.g. dichloromethane and chloroform. These solvents are used each alone or in mixtures.

The ratio of the aldehyde of formula (III) to the compound of formula (II) in the reaction mixture should be equimolar or more and is generally 1 to 40, preferably 5 to 25, moles of the aldehyde for one mole of the compound of formula (II). The pH of the reaction mixture is 7 or below in order not to interfere with the formation of the imine compound, an intermediate.

The imine compound obtained as an intermediate is then reduced to yield the intended compound of formula (I). The reduction is carried out either in the presence of reductants such as metal hydrides, e.g. sodium borohydride, sodium cyanoborohydride, lithium aluminum hydride, and lithium aluminum cyanohydride, or boranes or by using the nascent hydrogen generated by the reaction between metals such as zinc, zinc amalgam, tin, and iron and the acids such as acetic acid, hydrochloric acid, and sulfuric acid. The above-mentioned solvents can also be used in carrying out the reduction. When the reduction is carried out in the presence of a reductant it is preferable to add a dehydrating agent such as a molecular sieves or an acid anhydride. When a metal hydride is used as the reductant, it is preferable for promoting the reaction to keep the reaction system under acidic conditions of pH 7 or less. As examples of acids used for such a purpose, mention may be made of inorganic acids such as hydrogen chloride, hydrochloric acid, sulfuric acid, and nitric acid; Lewis acids such as magnesium chloride and ammonium sulfate; and organic acids such as formic acid, acetic acid, propionic acid, butyric acid, benzoic acid, phthalic acid, and p-toluenesulfonic acid.

In one of the preferred embodiments of this invention, the reaction between the compound of formula (II) and the aldehyde of formaula (III) is carried out under reducing conditions. The above-mentioned reaction conditions can also be used in this case. The reactions of formation and reduction of the imine intermediate are carried out at a temperature generally in the range of from −10° to 120° C., preferably from 10° to 85° C.

The isolation and purification of the intended compound of formula (I) are performed by any or a suitable combination of the customary techniques such as, for example, column chromatography using a silica gel, alumina, ion exchange resin, or activated carbon; recrystallization, precipitation by the pH adjustment, salting out with sodium chloride, and extraction with organic solvents.

Upon being treated with hydroxides, carbonates, or hydrogen carbonates of alkali metals, or alkaline earth metals; ammonia or organic amines, e.g. triethylamine and tributylamine, the compound of formula (I) in free acid form can be converted to the corresponding salts formed with the cyclic phosphoric acid moiety.

As examples of $N^6$-substituted CAMP's and salts thereof represented by the general formula (I), which are obtained according to the present invention, mention may be made of $N^6$-ethyl-CAMP, $N^6$-propyl-CAMP, $N^6$-isopropyl-CAMP, $N^6$-butyl-CAMP, $N^6$-isobutyl-CAMP, $N^6$-pentyl-CAMP, $N^6$-isopentyl-CAMP, $N^6$-neopentyl-CAMP, $N^6$-hexyl-CAMP, $N^6$-isohexyl-CAMP, $N^6$-heptyl-CAMP, $N^6$-isoheptyl-CAMP, $N^6$-octyl-CAMP, $N^6$-nonyl-CAMP, $N^6$-decyl-CAMP, $N^6$-undecyl-CAMP, $N^6$-dodecyl-CAMP, $N^6$-tridecyl-CAMP, $N^6$-tetradecyl-CAMP, $N^6$-benzyl-CAMP, $N^6$-p-methylbenzyl-CAMP, $N^6$-m-methylbenzyl-CAMP, $N^6$-p-chlorobenzyl-CAMP, $N^6$-p-hydroxybenzyl-CAMP, $N^6$-p-methoxybenzyl-CAMP, $N^6$-furfuryl-CAMP, and alkali metal salts thereof.

According to this invention, it is possible to prepare efficiently $N^6$-substituted 3′,5′-cyclic adenosine monophosphate and salts thereof which are intermediates in the preparation of $N^6$, 8-disubstituted 3′,5′-cyclic adenosine monophosphates with excellent pharmacological activities.

Hereunder the invention will be explained in more detail with reference to Examples, but the invention is not limited thereto.

EXAMPLE 1

Preparation of $N^6$-butyl-CAMP (A) Into 10 ml of acetic acid, was dissolved 1.03 g of tributylamine salt of CAMP. To the resulting solution, were added 1.8 ml of n-butyraldehyde and 127 mg of sodium cyanoborohydride. The mixture was stirred at room temperature. After 40 minutes and 140 minutes, to the mixture was added each time 127 mg of sodium cyanoborohydride. The mixture was stirred overnight. After addition of a small volume of water to the mixture, the solvent was removed by distillation under reduced pressure, leaving behind an oily substance. The oily substance was dissolved in a small volume of water, adjusted to pH 2 with 2 N hydrochloric acid, and adsorbed on an activated carbon column, 1.8×23 cm. After washing with water, the column was eluted with a methanol-water-28% ammonium hydroxide (10:10:1 by volume) mixture. The eluate was collected and evaporated to dryness under reduced pressure. The resulting caramel-like substance was dissolved in a small volume of methanol, then adjusted to pH 2 with 2 N hydrochloric acid, and fractionated as well as purified by silica gel thin layer chromatography (developing solvent: a methanol-chloroform (4:6 by volume) mixture) to collect by scraping the band (Rf≈0.4) of UV absorption corresponding to the intended compound. The collected fraction was extracted with methanol, and evaporated to dryness under reduced pressure to yield 700 mg (90% yield) of $N^6$-butyl-CAMP. The substance thus obtained was dissolved in 2 N sodium hydroxide solution, then adjusted to pH 2 with 2 N hydrochloric acid, and recrystallized to obtain a compound melting at 187°–189° C. (decomp.).

| Elementary analysis: | | | |
|---|---|---|---|
| | C | H | N |
| Found (%) | 42.26 | 5.22 | 17.61 |
| Calculated (%) for $C_{14}H_{20}N_5O_6P.\frac{1}{2}H_2O$ | 42.32 | 5.41 | 17.63 |

UV: $\lambda_{max.}^{0.1N\text{-}HCl}$ ($\epsilon$) 263 (19300) nm.

(B) Into 5 ml of acetic acid, was dissolved 527 mg of tributylamine salt of CAMP. After addition of 1 ml of n-butyraldehyde and 40 mg of sodium borohydride, the mixture was stirred at room temperature. After further addition of 230 mg of sodium borohydride, the mixture was again stirred overnight. The mixture was then treated as in (A) to yield 291 mg (74% yield) of $N^6$-butyl-CAMP, the intended product.

(C) Into 1 N sodium hydroxide solution, was dissolved by neutralization 1 g of CAMP. To the resulting solution, were added 5 ml of 5 M acetate buffer (pH 3.9), 10 ml of acetic acid, 5 ml of ethanol, 4 ml of n- butyraldehyde, 500 mg of zinc dust, and 100 mg of copper sulfate. To the mixture, while being heated at 80° C., were added, after 1 hour, 500 mg of zinc dust, then after 5 hours, 1.5 ml of n-butyraldehyde and 500 mg of zinc dust, and finally after 8 hours, 1 ml of n-butyraldehyde, 200 mg of copper sulfate, and 500 mg of zinc dust. After the successive addition, the mixture was allowed to react overnight at 80° C. The reaction mixture was filtered and the residue was washed with methanol and water. The filtrate and the washings were combined and concentrated. The concentrate was mixed with a small volume of water and 2 N hydrochloric acid and adsorbed on an activated carbon column, 1.8×24 cm. The column was washed with water and eluted with an ethanol-water-28% ammonium hydroxide (10:10:1 by volume) mixture. The eluate was evaporated to dryness under reduced pressure. The residue was treated as in Example 1 to yield 807 mg (69% yield) of $N^6$-butyl-CAMP.

EXAMPLE 2

Preparation of $N^6$-isobutyl-CAMP

Into 10 ml of acetic acid, was dissolved 1.03 g of tributylamine salt of CAMP. After addition of 2.8 ml of isobutyraldehyde and 130 mg of sodium cyanoborohydride, the mixture was stirred at room temperature. To the mixture, was further added 373 mg of sodium cyanoborohydride over a period of two days. The reaction mixture was mixed with a small volume of water and stripped of the solvent by distillation under reduced pressure. An oily substance which was left behind was dissolved in a small volume of water then adjusted to pH 2 with 2 N hydrochloric acid, and adsorbed on an activated carbon column, 1.8×22 cm. After washing with water, the column was eluted with a methanol-water-28% ammonium hydroxide (10:10:1 by volume) mixture. The eluate was evaporated under reduced pressure. The residue was dissolved in a small volume of methanol, then adjusted to pH 2 with 2 N hydrochloric acid, and fractionated as well as purified by silica gel thin layer chromatography (developing solution:methanol-chloroform=35:65 by volume). The band (Rf≈0.34) of UV absorption corresponding to the intended compound was collected by scraping and extracted with methanol. The extract was evaporated to dryness under reduced pressure to yield 333.2 mg (43.3% yield) of $N^6$-isobutyl-CAMP melting at 196°–199° C. (decomp.).

| | Elementary analysis: | | |
|---|---|---|---|
| | C | H | N |
| Found (%) | 42.15 | 5.20 | 17.50 |
| Calculated (%) for $C_{14}H_{20}N_5O_6P.\frac{1}{2} H_2O$ | 42.32 | 5.41 | 17.63 |

UV: $\lambda_{max}^{0.1N\text{-}HCl}$ ($\epsilon$) 262.5 (18800) nm.

EXAMPLE 3

Preparation of sodium salt of $N^6$-isobutyl-CAMP

Into 10 ml of acetic acid, was dissolved 1.03 g of tributylamine salt of CAMP. After addition of 1.8 ml of isobutyraldehyde and 50 mg of sodium borohydride, the mixture was stirred at room temperature. To the mixture, were added 0.4 ml of isobutyraldehyde and a total of 480 mg of sodium borohydride in 5 portions, each portion being about 100 mg, over a period of 2 days. The reaction mixture was mixed with a small volume of water and stripped of the solvent by distillation under reduced pressure. An oily substance which was left behind was dissolved in a small volume of water, then adjusted to pH 2 with 2 N hydrochloric acid, and adsorbed on an activated carbon column, 1.8×26 cm. After washing with water, the column was eluted with a methanol-water-28% ammonium hydroxide (10:10:1 by volume) mixture. The eluate was evaporated to dryness under reduced pressure. The residue was dissolved in a small volume of water, then adjusted to pH 10 with 2 N sodium hydroxide solution and fractionated as well as purified by silica gel thin layer chromatography (developing solvent: methanol-chloroform=4:6 by volume). The band (Rf≈0.43) of UV absorption corresponding to the intended compound was collected by scraping and extracted with methanol. The extract was evaporated to dryness under reduced pressure to yield 431 mg (53.6% yield) of sodium salt of $N^6$-isobutyl-CAMP. The salt thus obtained was dissolved in a small volume of water and adjusted to pH 2 with 2 N hydrochloric acid. Upon addition of ethanol to the solution, there was formed a white precipitate which substantially coincided with the $N^6$-isobutyl-CAMP of Example 2 in IR and UV absorption spectra and in melting point.

EXAMPLE 4

Preparation of $N^6$-n-octyl-CAMP (A) Into 10 ml of acetic acid, was dissolved 1.03 g of tributylamine salt of CAMP. After addition of 3.1 ml of n-octylaldehyde and 105 mg of sodium cyanoborohydride, the mixture was stirred at room temperature. After 2.5 hours and 5 hours, to the mixture were added respectively 130 mg and 40 mg of sodium cyanoborohydride. After 7 hours, a molecular sieves (4 A 1/16) was added and the mixture was further stirred overnight. The reaction mixture was filtered and the molecular sieves was washed with methanol. The filtrate and the washings were combined and stripped of the solvent by distillation under reduced pressure. The residue was suspended in a small volume of water, then adjusted to pH 2 with 2 N hydrochloric acid, and adsorbed on an activated carbon column, 1.8×21 cm. The column was washed with water and eluted with a methanol-water-28% ammonium hydroxide (10:10:1 by volume) mixture. The eluate was evaporated to dryness under reduced pressure. The residue was dissolved in a small volume of methanol and fractionated as well as purified by silica gel thin layer chromatography (developing solvent:methanol-chloroform=2:3 by volume). The band (Rf≈0.47) of UV absorption corresponding to the intended compound was collected by scraping and extracted with methanol. The extract was evaporated to dryness under reduced pressure to yield 645.5 mg (70.5% yield) of ammonium salt of $N^6$-n-octyl-CAMP. Free acid form of $N^6$-n-octyl-CAMP melting at 180°–182° C. was obtained by dissolving the salt in water and adjusting the resulting solution to pH 2 with 2 N hydrochloric acid.

| | Elementary analysis: | | |
|---|---|---|---|
| | C | H | N |
| Found (%) | 47.91 | 6.37 | 15.32 |
| Calculated (%) for $C_{18}H_{28}N_5O_6P.\frac{1}{2} H_2O$ | 48.0 | 6.49 | 15.55 |

UV: $\lambda_{max}^{0.1N\text{-}HCl}$ (ε) 263 (18200) nm.

(B) Into 15 ml of acetic acid, was dissolved 1.05 g of sodium salt of CAMP. After addition of 6.2 ml of n-octylaldehyde and 150 mg of sodium cyanoborohydride, the mixture was stirred at room temperature. After 2 hours, 4 hours, and 7 hours, to the mixture were added respectively 150 mg, 100 mg, and 100 mg of sodium cyanoborohydride. The stirring was further continued overnight. The reaction mixture was mixed with a small volume of water and stripped of the solvent by distillation under reduced pressure. The residue was suspended in a small volume of water and the suspension, after being adjusted to pH 2 with 2 N hydrochloric acid, was adsorbed on an activated carbon column, 1.8×24 cm. After washing with water, the column was eluted with a methanol-water-28% ammonium hydroxide (10:10:1 by volume) mixture and the eluate was evaporated to dryness under reduced pressure. The residue was dissolved in a small volume of methanol and fractionated as well as purified by silica gel thin layer chromatography (developing solvent:methanol-chloroform=2:3 by volume). The band (Rf≈0.47) of UV absorption corresponding to the intended compound was collected by scraping and extracted with methanol. The extract was evaporated to dryness under reduced pressure to yield 971.5 mg (73.4% yield) of ammonium salt of $N^6$-n-octyl-CAMP. Free acid form $N^6$-n-octyl-CAMP was obtained by dissolving the salt in water and adjusting the resulting solution to pH 2 with 2 N hydrochloric acid.

EXAMPLE 5

Preparation of $N^6$-benzyl-CAMP

Into 10 ml of acetic acid, was dissolved 1.03 g of tributylamine salt of CAMP. After addition of 2 ml of benzaldehyde and 110 mg of sodium cyanoborohydride, the mixture was stirred at room temperature. To the mixture, was further added 545 mg of sodium cyanoborohydride over a period of 2 days. The reaction mixture was mixed with a small volume of water and stripped of the solvent by distillation under reduced pressure. The residue was dissolved in a small volume of water, then adjusted to pH 2 with 2 N hydrochloric acid, and adsorbed on an activated carbon column, 1.8×23 cm. After washing with water, the column was eluted with a methanol-water-28% ammonium hydroxide (10:10:1 by volume) mixture, and the eluate was evaporated to dryness under reduced pressure. The residue was dissolved in methanol, then adjusted to pH 2 with 2 N hydrochloric acid, and fractionated as well as purified by silica gel thin layer chromatography (developing solvent:methanol-chloroform=2:3 by volume). The band (Rf≈0.42) of UV absorption corresponding to the intended compound was collected by scraping and extracted with methanol. The extract was evaporated to dryness under reduced pressure to yield 617.9 mg (73.6% yield) of $N^6$-benzyl-CAMP melting at 193°–195° C. (decomp.).

| Elementary analysis: | | | |
|---|---|---|---|
| | C | H | N |
| Found (%) | 46.50 | 4.66 | 15.84 |
| Calculated (%) for $C_{17}H_{18}N_5O_6P\cdot H_2O$ | 46.72 | 4.58 | 16.03 |

UV: $\lambda_{max}^{0.1N\text{-}HCl}$ (ε) 264 (19100) nm.

EXAMPLE 6

Preparation of sodium salt of $N^6$-furfuryl-CAMP

To 1.03 g of tributylamine salt of CAMP, were added 10 ml of methanol and 2 ml of acetic acid. The mixture was stirred to form a solution. To the solution, were added 2.7 ml of furfural and 126 mg of sodium cyanoborohydride. To the mixture, while being stirred at room temperature, was further added 756 mg of sodium cyanoborohydride over a period of 2 days. The reaction mixture was mixed with a small volume of water and stripped of the solvent by distillation under reduced pressure. The residue was dissolved in a small volume of water, then adjusted to pH 2 with 2 N hydrochloric acid, and adsorbed on an activated carbon column, 1.8×26 cm. After washing with water, the column was eluted with a methanol-water-28% ammonium hydroxide (10:10:1 by volume) mixture. The eluate was evaporated to dryness under reduced pressure. The residue was dissolved in a small volume of 1 N sodium hydroxide solution and fractionated as well as purified by silica gel thin layer chromatography (developing solvent:methanol-chloroform=3:7 by volume). The band (Rf≈0.14) of UV absorption corresponding to the intended compound was collected by scraping and extracted with methanol. The extract was evaporated to dryness under reduced pressure to yield 560 mg (65% yield) of sodium salt of $N^6$-furfuryl-CAMP having a melting point of 220°–223° C. (decomp.).

| Elementary analysis: | | | |
|---|---|---|---|
| | C | H | N |
| Found (%) | 39.27 | 3.67 | 14.96 |
| Calculated (%) for $C_{15}H_{15}N_5O_7PNa\cdot 3/2\ H_2O$ | 39.31 | 3.95 | 15.28 |

UV: $\lambda_{max}^{0.1N\text{-}HCl}$ (ε) 264 (17050) nm.

What is claimed is:

1. A process for the preparation of an $N^6$-substituted 3′,5′-cyclic adenosine monophosphate or a salt thereof represented by the following formula

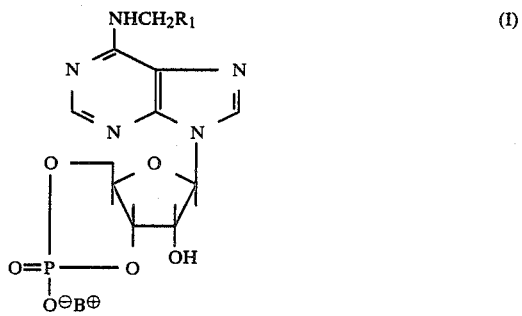

wherein $R_1$ represents a straight chain alkyl group of 1 to 13 carbon atoms, a branched chain alkyl group of 3 to 13 carbon atoms or an aromatic group and $B^\oplus$ represents a hydrogen ion or an alkali metal ion, which comprises allowing a 3′,5′-cyclic adenosine monophosphate or a salt thereof represented by the following formula

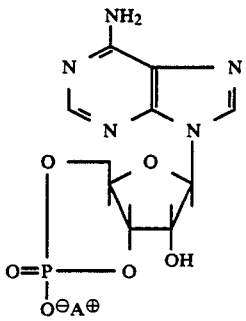

wherein A⊕ represents a hydrogen ion, alkali metal ion, organic ammonium ion, or ammonium ion, to react with an aldehyde represented by the following formula

R₁CHO    (III)

wherein R₁ is as defined above, under acidic conditions at a temperature in the range of −10° to 120° C., and at a molar ratio of the compound (II) to the compound (III) in the range of 1:1 to 1:40, and reducing the resulting compound with a metal hydride or nascent hydrogen.

2. A method according to claim 1, wherein A⊕ is H+, Na+, K+, triethylammonium, tributylammonium, or ammonium.

3. A method according to claim 1, wherein the aromatic group represented by R₁ is a phenyl, furyl, tolyl, hydroxyphenyl, methoxyphenyl, or chlorophenyl group.

4. A method according to claim 1, wherein B⊕ is H+, Na+, or K+.

5. A method according to claim 1, wherein the solvent is at least one member selected from the group consisting of water, methanol, ethanol, tetrahydrofuran, dioxane, dimethylformamide, dimethylacetamide, acetic acid, ethyl acetate, butyric acid, dichloromethane, and chloroform.

6. A method according to claim 1, wherein the reaction temperature is in the range of from 10° to 85° C.

* * * * *